US010595628B2

(12) United States Patent
Jimenez et al.

(10) Patent No.: US 10,595,628 B2
(45) Date of Patent: Mar. 24, 2020

(54) ORAL CARE IMPLEMENT

(71) Applicant: Colgate-Palmolive Company, New York, NY (US)

(72) Inventors: Eduardo Jimenez, Manalapan, NJ (US); Kenneth Waguespack, North Brunswick, NJ (US); Robert Moskovich, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 295 days.

(21) Appl. No.: 15/539,411

(22) PCT Filed: Dec. 23, 2014

(86) PCT No.: PCT/US2014/072073
§ 371 (c)(1),
(2) Date: Jun. 23, 2017

(87) PCT Pub. No.: WO2016/105372
PCT Pub. Date: Jun. 30, 2016

(65) Prior Publication Data
US 2018/0008035 A1 Jan. 11, 2018

(51) Int. Cl.
*A46B 15/00* (2006.01)
*A46B 9/04* (2006.01)
*A61B 17/24* (2006.01)

(52) U.S. Cl.
CPC ............ *A46B 15/0081* (2013.01); *A46B 9/04* (2013.01); *A61B 17/244* (2013.01); *A46B 2200/1066* (2013.01)

(58) Field of Classification Search
CPC ........ A46B 15/0081; A46B 2200/1066; A46B 9/04; A61B 17/244
See application file for complete search history.

(56) References Cited

U.S. PATENT DOCUMENTS 758,764 A 5/1904 MacLeod
846,900 A 3/1907 Bloom
(Continued)

FOREIGN PATENT DOCUMENTS

AR 71556 10/2003
AR 80042 11/2009
(Continued)

OTHER PUBLICATIONS

International Search Report and the Written Opinion issued in International Application PCT/US2010/046806 dated Mar. 16, 2011.
(Continued)

*Primary Examiner* — Marc Carlson

(57) ABSTRACT

An oral care implement having a head with a soft tissue cleanser thereon. In one aspect, the invention can be an oral care implement including a handle and a head coupled to the handle, the head comprising a front surface; a rear surface opposite the front surface; a peripheral surface extending between the rear surface and the front surface; a first elastomeric soft tissue cleanser comprising a bumper portion that extends along the peripheral surface, the bumper portion comprising an undulating upper edge that includes a plurality of high points protruding above the rear surface and a plurality of low points located at or below the rear surface; and a plurality of tooth cleaning elements extending from the front surface.

20 Claims, 7 Drawing Sheets

(56) References Cited

U.S. PATENT DOCUMENTS

| | | |
|---|---|---|
| 1,125,532 A | 1/1915 | Himmel |
| 1,901,230 A | 3/1933 | Palmer |
| 1,924,152 A | 8/1933 | Coney et al. |
| 2,117,174 A * | 5/1938 | Jones .................. A46B 9/04 15/110 |
| 2,161,349 A | 6/1939 | Hadden |
| 2,186,005 A | 1/1940 | Casto |
| 2,305,461 A | 12/1942 | Spyra |
| D273,635 S | 5/1984 | Stocchi |
| 4,517,701 A | 5/1985 | Stanford, Jr. |
| 4,958,402 A | 9/1990 | Weihrauch |
| 5,144,712 A | 9/1992 | Hansel et al. |
| 5,339,482 A | 8/1994 | Desimone et al. |
| 5,392,483 A | 2/1995 | Heinzelman et al. |
| 5,584,690 A | 12/1996 | Maassarani |
| 5,604,951 A | 2/1997 | Shipp |
| 5,628,082 A * | 5/1997 | Moskovich .............. A46B 5/02 15/110 |
| 5,651,158 A | 7/1997 | Halm |
| D390,706 S | 2/1998 | Hohlbein et al. |
| 5,735,012 A | 4/1998 | Heinzelman et al. |
| 5,746,532 A | 5/1998 | Megill et al. |
| 5,758,383 A | 6/1998 | Hohlbein |
| 5,781,958 A | 7/1998 | Meessmann et al. |
| 5,799,353 A | 9/1998 | Yamamoto et al. |
| 5,802,656 A | 9/1998 | Dawson et al. |
| 5,839,149 A | 11/1998 | Scheier et al. |
| D404,205 S | 1/1999 | Hohlbein |
| D404,206 S | 1/1999 | Hohlbein |
| 5,862,559 A | 1/1999 | Hunter |
| 5,863,102 A | 1/1999 | Waguespack et al. |
| 5,908,038 A | 6/1999 | Bennett |
| 5,915,868 A | 6/1999 | Frazell |
| 5,930,860 A | 8/1999 | Shipp |
| 5,946,758 A | 9/1999 | Hohlbein et al. |
| 5,967,152 A | 10/1999 | Rimkus |
| 5,970,564 A | 10/1999 | Inns et al. |
| 5,984,935 A | 11/1999 | Budei et al. |
| 5,991,958 A | 11/1999 | Hohlbein |
| 6,015,293 A | 1/2000 | Rimkus |
| 6,032,313 A | 3/2000 | Tsang |
| 6,041,468 A | 3/2000 | Chen et al. |
| 6,073,299 A | 6/2000 | Hohlbein |
| 6,088,870 A | 7/2000 | Hohlbein |
| D429,887 S | 8/2000 | Hohlbein et al. |
| 6,099,780 A | 8/2000 | Gellert |
| 6,131,228 A | 10/2000 | Chen et al. |
| 6,178,583 B1 | 1/2001 | Volpenhein |
| 6,234,798 B1 | 5/2001 | Salazar et al. |
| 6,276,021 B1 | 8/2001 | Hohlbein |
| 6,292,973 B1 | 9/2001 | Moskovich et al. |
| D450,457 S | 11/2001 | Hohlbein |
| D450,929 S | 11/2001 | Angelini et al. |
| 6,314,606 B1 | 11/2001 | Hohlbein |
| D451,286 S | 12/2001 | Hohlbein |
| D456,138 S | 4/2002 | Hohlbein |
| D456,139 S | 4/2002 | Hohlbein |
| 6,370,726 B1 | 4/2002 | Kini et al. |
| D457,323 S | 5/2002 | Hohlbein |
| 6,397,425 B1 | 6/2002 | Szczech et al. |
| 6,408,476 B1 | 6/2002 | Cann |
| 6,421,867 B1 | 7/2002 | Weihrauch |
| D461,313 S | 8/2002 | Hohlbein |
| 6,442,786 B2 | 9/2002 | Halm |
| 6,442,787 B2 | 9/2002 | Hohlbein |
| D464,133 S | 10/2002 | Barnett et al. |
| 6,463,618 B1 | 10/2002 | Zimmer |
| D474,608 S | 5/2003 | Hohlbein |
| 6,564,416 B1 | 5/2003 | Claire et al. |
| 6,596,213 B2 | 6/2003 | Swenson |
| 6,595,087 B2 | 7/2003 | Whalen et al. |
| 6,599,048 B2 | 7/2003 | Kuo |
| 6,601,272 B2 | 8/2003 | Stvartak et al. |
| 6,658,688 B2 | 12/2003 | Gavney, Jr. |
| D486,649 S | 2/2004 | Sprosta et al. |
| 6,687,940 B1 | 2/2004 | Gross et al. |
| 6,749,788 B1 | 6/2004 | Holden et al. |
| 6,766,549 B2 | 7/2004 | Klupt |
| 6,792,642 B2 | 9/2004 | Wagstaff |
| 6,820,299 B2 | 11/2004 | Gavney, Jr. |
| 6,820,300 B2 | 11/2004 | Gavney, Jr. |
| 6,859,969 B2 | 3/2005 | Gavney, Jr. et al. |
| D503,538 S | 4/2005 | Desalvo |
| 6,886,207 B1 | 5/2005 | Solanki |
| 6,889,405 B2 | 5/2005 | Ritrovato et al. |
| 6,919,038 B2 | 7/2005 | Meyer et al. |
| 6,957,469 B2 | 10/2005 | Davies |
| D511,249 S | 11/2005 | Hohlbein |
| 6,972,106 B2 | 12/2005 | Huber et al. |
| D513,882 S | 1/2006 | Hohlbein et al. |
| 6,983,507 B2 | 1/2006 | McDougall |
| D514,320 S | 2/2006 | Hohlbein |
| D514,812 S | 2/2006 | Hohlbein et al. |
| 6,996,870 B2 | 2/2006 | Hohlbein |
| D516,819 S | 3/2006 | Hohlbein |
| D517,812 S | 3/2006 | Hohlbein et al. |
| D517,813 S | 3/2006 | Hohlbein et al. |
| 7,007,332 B2 | 3/2006 | Hohlbein |
| 7,020,928 B2 | 4/2006 | Hohlbein |
| D520,753 S | 5/2006 | Hohlbein |
| 7,047,591 B2 | 5/2006 | Hohlbein |
| 7,069,615 B2 | 7/2006 | Gavney, Jr. |
| 7,073,225 B1 | 7/2006 | Ford |
| D526,487 S | 8/2006 | Chenvainu et al. |
| 7,083,756 B2 | 8/2006 | Strahler |
| 7,089,621 B2 | 8/2006 | Hohlbein |
| D527,528 S | 9/2006 | Hohlbein |
| D528,803 S | 9/2006 | Hohlbein |
| D532,202 S | 11/2006 | Hohlbein |
| D532,607 S | 11/2006 | Hohlbein |
| 7,143,462 B2 | 12/2006 | Hohlbein |
| 7,146,675 B2 | 12/2006 | Ansari et al. |
| 7,168,125 B2 | 1/2007 | Hohlbein |
| 7,181,799 B2 | 2/2007 | Gavney, Jr. et al. |
| 7,182,542 B2 | 2/2007 | Hohlbein |
| 7,213,288 B2 | 5/2007 | Hohlbein |
| 7,219,384 B2 | 5/2007 | Hohlbein |
| 7,273,327 B2 | 9/2007 | Hohlbein et al. |
| D557,504 S | 12/2007 | Hohlbein |
| D557,505 S | 12/2007 | Hohlbein |
| 7,322,067 B2 | 1/2008 | Hohlbein |
| D562,560 S | 2/2008 | Hohlbein |
| 7,331,731 B2 | 2/2008 | Hohlbein et al. |
| 7,354,112 B2 | 4/2008 | Fischer et al. |
| 7,383,619 B2 | 6/2008 | Gross et al. |
| 7,386,909 B2 | 6/2008 | Hohlbein |
| 7,415,788 B2 | 8/2008 | Little |
| 7,458,125 B2 | 12/2008 | Hohlbein |
| 7,472,448 B2 | 1/2009 | Hohlbein et al. |
| 7,478,959 B2 | 1/2009 | Hohlbein |
| 7,480,955 B2 | 1/2009 | Hohlbein et al. |
| D589,260 S | 3/2009 | Hohlbein |
| 7,540,844 B2 | 6/2009 | Muser |
| D598,199 S | 8/2009 | Russell et al. |
| D598,654 S | 8/2009 | Huang |
| D599,556 S | 9/2009 | Russell et al. |
| 7,614,111 B2 | 11/2009 | Moskovich et al. |
| D609,915 S | 2/2010 | Erskine-Smith et al. |
| D612,611 S | 3/2010 | Brown, Jr. et al. |
| 7,712,175 B2 | 5/2010 | Blanchard et al. |
| 7,721,376 B2 | 5/2010 | Hohlbein et al. |
| 7,722,274 B2 | 5/2010 | Hohlbein et al. |
| 7,735,174 B2 | 6/2010 | Hohlbein et al. |
| D623,415 S | 9/2010 | Geiberger |
| 7,788,756 B2 | 9/2010 | Kraemer |
| 7,845,042 B2 | 12/2010 | Moskovich et al. |
| 7,854,036 B2 | 12/2010 | Georgi |
| 7,937,794 B2 | 5/2011 | Huber et al. |
| 7,954,191 B2 | 6/2011 | Hohlbein |
| 7,958,589 B2 | 6/2011 | Braun et al. |
| 7,975,343 B2 | 7/2011 | Hohlbein et al. |
| 7,975,346 B2 | 7/2011 | Moskovch et al. |
| 7,979,947 B2 | 7/2011 | Storkel et al. |
| 8,032,991 B2 | 10/2011 | Lawless |

(56) References Cited

U.S. PATENT DOCUMENTS

| | | | |
|---|---|---|---|
| 8,042,217 B2 | 10/2011 | Sorrentino | |
| 8,046,864 B2 | 11/2011 | Baertschi et al. | |
| 8,060,972 B2 | 11/2011 | Geiberger et al. | |
| 8,083,980 B2 | 12/2011 | Huber et al. | |
| 8,201,298 B2* | 6/2012 | Hohlbein | A46B 15/0032 15/110 |
| 8,239,996 B2 | 8/2012 | Garber et al. | |
| 8,307,488 B2 | 11/2012 | Pfenniger et al. | |
| 8,327,492 B2 | 12/2012 | Cann | |
| 8,332,982 B2 | 12/2012 | Braun et al. | |
| 8,332,985 B2 | 12/2012 | Solanki | |
| 8,382,208 B2 | 2/2013 | Baertschi et al. | |
| 8,448,284 B2 | 5/2013 | Gross et al. | |
| 8,448,287 B2 | 5/2013 | Ponzini et al. | |
| 8,458,846 B2 | 6/2013 | Schamberg et al. | |
| 8,484,789 B2 | 7/2013 | Claire-Zimmet et al. | |
| 8,500,766 B2 | 8/2013 | Jimenez et al. | |
| 8,528,148 B2 | 9/2013 | Brown, Jr. et al. | |
| 8,561,247 B2* | 10/2013 | Moskovich | A46B 5/0029 15/167.1 |
| 8,595,886 B2 | 12/2013 | Edelstein et al. | |
| 8,601,635 B2 | 12/2013 | Goldman et al. | |
| 8,608,251 B2 | 12/2013 | Nirwing et al. | |
| 8,621,698 B2 | 1/2014 | Chenvainu et al. | |
| 8,631,534 B2 | 1/2014 | Blanchard et al. | |
| 8,732,890 B2 | 5/2014 | Mohr et al. | |
| 8,739,351 B2 | 6/2014 | Kling et al. | |
| 8,776,302 B2 | 7/2014 | Baertschi et al. | |
| 8,813,292 B2 | 8/2014 | Driesen et al. | |
| 9,462,877 B2* | 10/2016 | Xi | A46B 5/0029 |
| D808,659 S * | 1/2018 | Ballmaier | D4/108 |
| 10,039,370 B2* | 8/2018 | Lee | A46B 9/04 |
| 2002/0017003 A1 | 2/2002 | Kramer et al. | |
| 2002/0138928 A1 | 10/2002 | Calabrese | |
| 2003/0077107 A1* | 4/2003 | Kuo | A46B 15/0002 401/278 |
| 2003/0163881 A1 | 9/2003 | Driesen et al. | |
| 2003/0178745 A1 | 9/2003 | Scarabelli et al. | |
| 2003/0178885 A1 | 9/2003 | Weihrauch | |
| 2004/0025275 A1 | 2/2004 | Moskovich et al. | |
| 2004/0107521 A1 | 6/2004 | Chan et al. | |
| 2004/0134007 A1 | 7/2004 | Davies | |
| 2005/0000049 A1* | 1/2005 | Hohlbein | A46B 9/026 15/111 |
| 2005/0166343 A1 | 8/2005 | Gavney, Jr. | |
| 2005/0210612 A1 | 9/2005 | Hohlbein et al. | |
| 2006/0010628 A1* | 1/2006 | Moskovich | A46B 15/0055 15/111 |
| 2006/0048314 A1 | 3/2006 | Kressner | |
| 2006/0048323 A1 | 3/2006 | Rueb | |
| 2006/0064827 A1 | 3/2006 | Chan | |
| 2006/0123574 A1 | 6/2006 | Storkel et al. | |
| 2006/0236477 A1 | 10/2006 | Gavney, Jr. | |
| 2006/0236478 A1 | 10/2006 | Hohlbein et al. | |
| 2006/0248667 A1 | 11/2006 | Kraemer | |
| 2007/0151058 A1 | 7/2007 | Kraemer et al. | |
| 2007/0169295 A1 | 7/2007 | Winter et al. | |
| 2007/0265555 A1 | 11/2007 | Deng | |
| 2007/0283517 A1 | 12/2007 | Blanchard et al. | |
| 2007/0283518 A1* | 12/2007 | Blanchard | A46B 9/025 15/167.1 |
| 2008/0086827 A1* | 4/2008 | Waguespack | A46B 5/0025 15/105 |
| 2009/0007357 A1 | 1/2009 | Meadows et al. | |
| 2009/0038097 A1 | 2/2009 | Geiberger | |
| 2009/0158543 A1 | 6/2009 | Lee | |
| 2009/0255077 A1 | 10/2009 | Mori et al. | |
| 2010/0043162 A1 | 2/2010 | Kling et al. | |
| 2010/0058550 A1 | 3/2010 | Ballmaier et al. | |
| 2010/0088836 A1 | 4/2010 | Kirchhofer et al. | |
| 2010/0101037 A1 | 4/2010 | Hilfiker et al. | |
| 2010/0115724 A1 | 5/2010 | Huang | |
| 2010/0180392 A1 | 7/2010 | Binet et al. | |
| 2010/0223746 A1 | 9/2010 | Mueller | |
| 2010/0263149 A1 | 10/2010 | Ballmaier et al. | |
| 2010/0306941 A1 | 12/2010 | Erskine-Smith et al. | |
| 2011/0030160 A1 | 2/2011 | Knutzen et al. | |
| 2011/0047736 A1* | 3/2011 | Jimenez | A46B 9/04 15/167.2 |
| 2011/0138560 A1 | 6/2011 | Vitt et al. | |
| 2011/0152909 A1* | 6/2011 | Jimenez | A61B 17/244 606/161 |
| 2011/0219558 A1 | 9/2011 | Vitt et al. | |
| 2011/0109149 A1 | 12/2011 | Loetscher et al. | |
| 2012/0034576 A1 | 2/2012 | Mostafa | |
| 2012/0174328 A1* | 7/2012 | Moskovich | A46B 9/04 15/106 |
| 2012/0192369 A1 | 8/2012 | Mohr et al. | |
| 2013/0007968 A1 | 1/2013 | Driesen et al. | |
| 2013/0036566 A1 | 2/2013 | Schlatter | |
| 2013/0139338 A1 | 6/2013 | Hess et al. | |
| 2013/0269128 A1 | 10/2013 | Jimenez | |
| 2013/0276252 A1* | 10/2013 | Xi | A46B 5/0029 15/105 |
| 2013/0291320 A1 | 11/2013 | Kirchhofer et al. | |
| 2013/0333126 A1 | 12/2013 | Miller | |
| 2014/0047656 A1 | 2/2014 | Newman et al. | |
| 2014/0158152 A1 | 6/2014 | Kirchhofer et al. | |
| 2014/0173838 A1 | 6/2014 | Dickie et al. | |
| 2014/0173853 A1 | 6/2014 | Kirchhofer et al. | |
| 2014/0298605 A1 | 10/2014 | Ivory | |
| 2014/0310901 A1 | 10/2014 | Geiberger et al. | |
| 2014/0325773 A1 | 11/2014 | Hohlbein | |
| 2016/0270520 A1* | 9/2016 | Lee | A46B 9/04 |
| 2017/0367473 A1* | 12/2017 | Jimenez | A46B 9/04 |

FOREIGN PATENT DOCUMENTS

| | | |
|---|---|---|
| BR | 7900283 | 8/2000 |
| BR | DI 6601454-9 | 4/2006 |
| BR | DI 6702593 | 8/2007 |
| BR | DI 6805210-3 | 11/2008 |
| BR | DI 6902120-1 | 5/2009 |
| BR | DI 6903329-3 | 8/2009 |
| BR | DI 6903330-7 | 8/2009 |
| BR | DI 6904386 | 11/2009 |
| BR | DI 7102178-7 | 4/2011 |
| BR | 30 2013 000448-1 | 2/2013 |
| BR | DI 6401609-9 | 5/2014 |
| CH | 215110 | 6/1941 |
| CN | 3372860D | 6/2004 |
| CN | 3372861D | 6/2004 |
| CN | 2732059 | 10/2005 |
| CN | 300704339 | 10/2007 |
| CN | 201294969 | 8/2009 |
| CN | 201518876 | 7/2010 |
| CN | 201518877 | 7/2010 |
| CN | 201518880 | 7/2010 |
| CN | 201528796 | 7/2010 |
| CN | 201541995 | 8/2010 |
| CN | 201541996 | 8/2010 |
| CN | 201541997 | 8/2010 |
| CN | 201550827 | 8/2010 |
| CN | 301406316 S | 12/2010 |
| CN | 301421505 S | 12/2010 |
| CN | 201814085 | 5/2011 |
| CN | 201986933 | 9/2011 |
| CN | 301763519 | 12/2011 |
| CN | 30198826 | 5/2012 |
| CN | 302058056 | 9/2012 |
| CN | 302225957 S | 12/2012 |
| CN | 302328863 S | 2/2013 |
| CN | 202800555 | 3/2013 |
| CN | 103005839 | 4/2013 |
| CN | 203194906 | 9/2013 |
| CN | 203220069 | 10/2013 |
| CN | 203220073 | 10/2013 |
| CN | 203252150 | 10/2013 |
| CN | 302956580 S | 10/2014 |
| DE | 19858102 | 6/2000 |
| DE | 202005009026 | 10/2005 |
| DE | 102006016939 | 5/2007 |

(56) References Cited

FOREIGN PATENT DOCUMENTS

| | | |
|---|---|---|
| DE | 102006005616 | 8/2007 |
| DE | 102006024874 | 11/2007 |
| DE | 202008016004 | 2/2009 |
| EM | 000366984-0001 | 7/2005 |
| EM | 000638028-0002 | 12/2006 |
| EM | 001975079-0005 | 1/2012 |
| EM | 002163675-0002 | 1/2013 |
| EM | 002163675-0003 | 1/2013 |
| EM | 002212522-0004 | 4/2013 |
| EM | 002212522-0012 | 4/2013 |
| EM | 002424069-0001 | 3/2014 |
| EP | 0716821 | 6/1996 |
| EP | 0769920 | 9/2003 |
| EP | 2810581 | 12/2014 |
| ES | 1063617 | 11/2006 |
| IT | 2010PDO000035-0019 | 10/2010 |
| JP | H08164025 | 6/1996 |
| JP | 10042957 | 8/1996 |
| JP | D1314270 | 10/2007 |
| KR | 20040032038 | 4/2004 |
| KR | 838174 | 6/2007 |
| KR | 20-2012-0005449 | 7/2012 |
| MX | 32553 | 11/2009 |
| MX | 36113 | 4/2011 |
| MX | 36650 | 4/2011 |
| RU | 55985 | 1/2005 |
| RU | 79787 | 10/2011 |
| RU | 80086 | 11/2011 |
| RU | 81915 | 6/2012 |
| WO | WO1995/06420 | 3/1995 |
| WO | WO1995/10959 | 4/1995 |
| WO | WO1999/023910 | 5/1999 |
| WO | WO1999/55514 | 11/1999 |
| WO | WO1999/65358 | 12/1999 |
| WO | WO2000/49911 | 8/2000 |
| WO | WO2001/17392 | 3/2001 |
| WO | WO2001/29128 | 4/2001 |
| WO | WO2001/45573 | 6/2001 |
| WO | WO2001/182741 | 11/2001 |
| WO | WO2004/043669 | 5/2004 |
| WO | WO2005/122827 | 12/2005 |
| WO | WO2008/017996 | 2/2008 |
| WO | WO2011/070549 | 6/2011 |
| WO | WO2012/017923 | 2/2012 |
| WO | WO2012/115035 | 8/2012 |
| WO | WO2012/176741 | 12/2012 |
| WO | WO2013/031685 | 3/2013 |

OTHER PUBLICATIONS

International Search Report and the Written Opinion issued in International Application PCT/US2012/070760 dated Oct. 14, 2013.
International Search Report and the Written Opinion issued in International Application PCT/US2014/072073 dated Sep. 11, 2015.

* cited by examiner

ORAL CARE IMPLEMENT

BACKGROUND

A toothbrush is used to clean the teeth by removing plaque and debris from the tooth surfaces. Toothbrushes have a handle for gripping and a head which is inserted into a user's mouth for tooth and oral surface cleaning. The head typically has bristles formed of nylon and sometimes also cleaning elements formed from elastomeric materials to perform the cleaning function. Furthermore, some toothbrushes have been developed that include a tongue or soft tissue cleanser formed of an elastomeric material on the opposite surface of the head relative to the bristles. Conventional toothbrushes may also include a handle and/or thumb grip that is formed with elastomeric materials for ease and comfort during handling and use. In conventional toothbrushes the tongue or soft tissue cleanser is only positioned on the rear surface of the head and thus there are limits to the possible variations for the design of the tongue or soft tissue cleanser and its cleaning effectiveness. Thus, a need exists for a toothbrush or other oral care implement that has soft tissue cleaning features that are aesthetically pleasing and more effective at removing bacteria from a user's tongue and soft tissue surfaces.

BRIEF SUMMARY

Exemplary embodiments according to the present disclosure are directed to an oral care implement that may include a handle and a head. The head may have a front surface, a rear surface, and a peripheral surface extending therebetween. An elastomeric soft tissue cleanser may be positioned along the peripheral surface of the head such that an undulating upper edge of the elastomeric soft tissue cleanser has high points that protrude beyond the rear surface of the head. The head may also include tooth cleaning elements extending from the front surface.

In one embodiment, the invention can be an oral care implement comprising: a handle; and a head coupled to the handle, the head comprising: a front surface; a rear surface opposite the front surface; a peripheral surface extending between the rear surface and the front surface; a first elastomeric soft tissue cleanser comprising a bumper portion that extends along the peripheral surface, the bumper portion comprising an undulating upper edge that includes a plurality of high points protruding above the rear surface and a plurality of low points located at or below the rear surface; and a plurality of tooth cleaning elements extending from the front surface.

In another embodiment, the invention can be an oral care implement comprising: a handle; a head coupled to the handle, the head comprising: a front surface; a rear surface opposite the front surface; a peripheral surface extending between the rear surface and the front surface, the peripheral surface and the rear surface intersecting to form a perimeter of the rear surface of the head; a base formed of a hard material, the base comprising an exposed annular surface that forms a portion of the rear surface of the head; a first elastomeric soft tissue cleanser coupled to the base, the first elastomeric soft tissue cleanser comprising a bumper portion on the peripheral surface, the bumper portion comprising a plurality of lower portions on the peripheral surface and a plurality of raised portions protruding above the rear surface along the perimeter; a second elastomeric soft tissue cleanser coupled to the base on the rear surface of the head, the exposed annular surface of the base circumscribing the second elastomeric soft tissue cleanser, the second elastomeric soft tissue cleanser comprising a plurality of protuberances that extend from the rear surface; the first and second elastomeric soft tissue cleansers being separate and distinct components from one another; and a plurality of tooth cleaning elements extending from the front surface.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
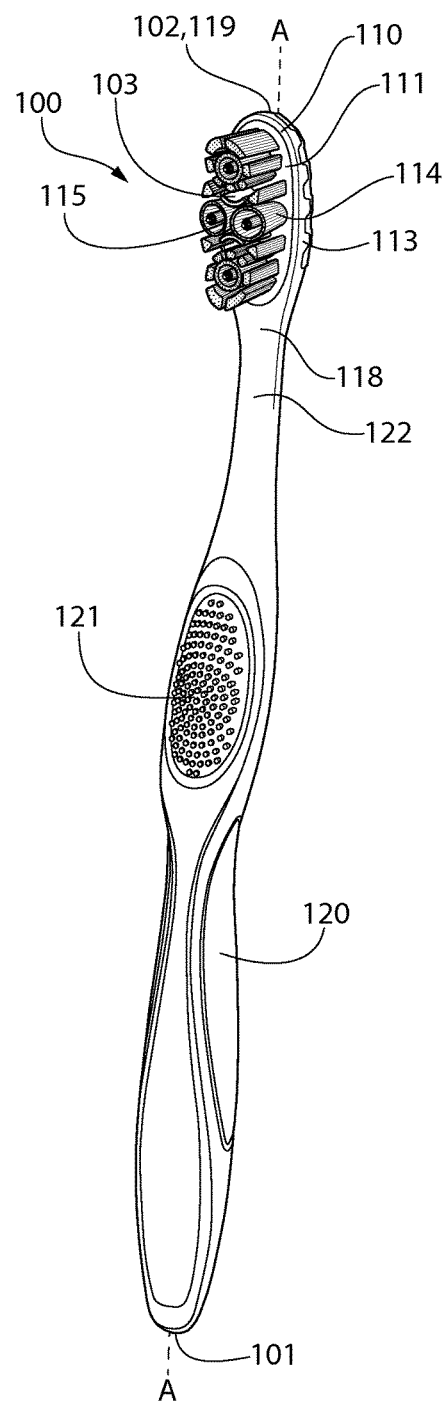
FIG. 1 is front perspective view of an oral care implement in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Figure 2:
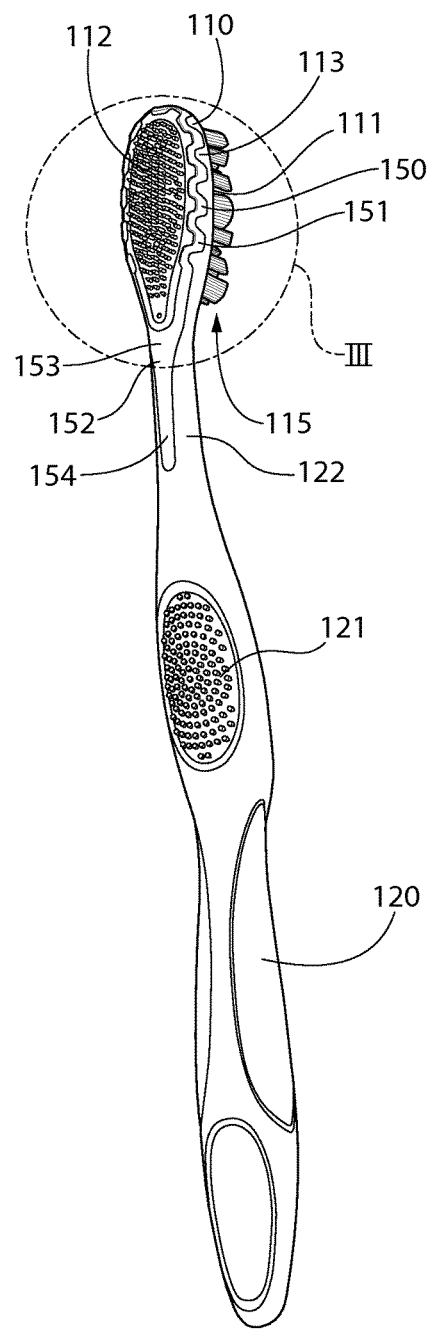
FIG. 2 is a rear perspective view of the oral care implement of FIG. 1.

Referring first to FIGS. 1 and 2 concurrently, an oral care implement 100 is illustrated in accordance with one embodiment of the present invention. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements, or any other type of implement that is commonly used for oral care. Thus, it is to be understood that the inventive concepts discussed herein can be applied to any type of oral care implement unless a specific type of oral care implement is specified in the claims.

The oral care implement 100, which generally comprises a head 110 and a handle 120, extends from a proximal end 101 to a distal end 102 along a longitudinal axis A-A. The head 110 extends from a proximal end 118 to a distal end 119 along a longitudinal axis that is coextensive with the longitudinal axis A-A of the oral care implement 100. Furthermore, in the exemplified embodiment the distal end 102 of the oral care implement 100 is the same as the distal end 119 of the head 110.

The handle 120 is an elongated structure that provides the mechanism by which the user can hold and manipulate the oral care implement 100 during use. In the exemplified embodiment, the handle 120 is generically depicted having various contours for user comfort. Of course, the invention is not to be limited by the specific shape illustrated for the handle 120 in all embodiments and in certain other embodiments the handle 120 can take on a wide variety of shapes, contours, and configurations, none of which are limiting of the present invention unless so specified in the claims.

In the exemplified embodiment, the handle 120 is formed of a hard or rigid plastic material, such as for example without limitation polymers and copolymers of ethylene, propylene, butadiene, vinyl compounds, and polyesters such as polyethylene terephthalate. The handle 120 also includes a grip 121 that is formed of a resilient/elastomeric material. In the exemplified embodiment the grip 121 is molded over a portion of the handle 120 that is typically gripped by a user's thumb and forefinger during use. Furthermore, it should be appreciated that additional regions of the handle 120 can be overmolded with the resilient/elastomeric material to enhance the gripability of the handle 120 during use. For example, portions of the handle 120 that are typically gripped by a user's palm during use may be overmolded with a thermoplastic elastomer or other resilient material to further increase comfort to a user. Furthermore, materials other than those noted above can be used to form the handle 120, including metal, wood, or any other desired material that has sufficient structural rigidity to permit a user to grip the handle 120 and manipulate the oral care implement 100 during toothbrushing.

The head 110 of the oral care implement 100 is coupled to the handle 120 and comprises a front surface 111 and an opposing rear surface 112. Furthermore, the head 110 comprises a peripheral surface 113 extending between the rear surface 112 and the front surface 111. In the exemplified embodiment, the head 110 is formed integrally with the handle 120 as a single unitary structure using a molding, milling, machining, or other suitable process. However, in other embodiments the handle 120 and the head 110 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Thus, the head 110 may, in certain embodiments, be formed of any of the rigid plastic materials described above as being used for forming the handle 120, although the invention is not to be so limited in all embodiments and other materials that are commonly used during toothbrush head manufacture may also be used.

The oral care implement 100 also comprises a plurality of tooth cleaning elements 115 extending from the front surface 111 of the head 110. The invention is not to be limited by the structure, pattern, orientation, and material of the tooth cleaning elements 115 in all embodiments. Furthermore, where it does not conflict with the other disclosure provided herein or the claims, it should be appreciated that the term "tooth cleaning elements" may be used in a generic sense to refer to any structure that can be used to clean, polish, or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, polybutylene terephthalate (PBT) bristles, spiral bristles, rubber bristles, elastomeric protrusions, flexible polymer protrusions, combinations thereof, and/or structures containing such materials or combinations. Thus, any combination of these tooth cleaning elements may be used within the tooth cleaning elements 115 in some embodiments. Furthermore, where bristles are used for one or more of the tooth cleaning elements 115, such bristles can be tapered, end-rounded, spiral, or the like.

In embodiments that use elastomeric materials to form one or more of the tooth cleaning elements 115, suitable elastomeric materials may include any biocompatible resilient material suitable for uses in an oral hygiene apparatus. To provide optimum comfort as well as cleaning benefits, the elastomeric material of any such tooth cleaning element may have a hardness property in the range of A10 to A70 Shore hardness in one embodiment, or A8 to A25 Shore hardness in another embodiment. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

Figure 4:
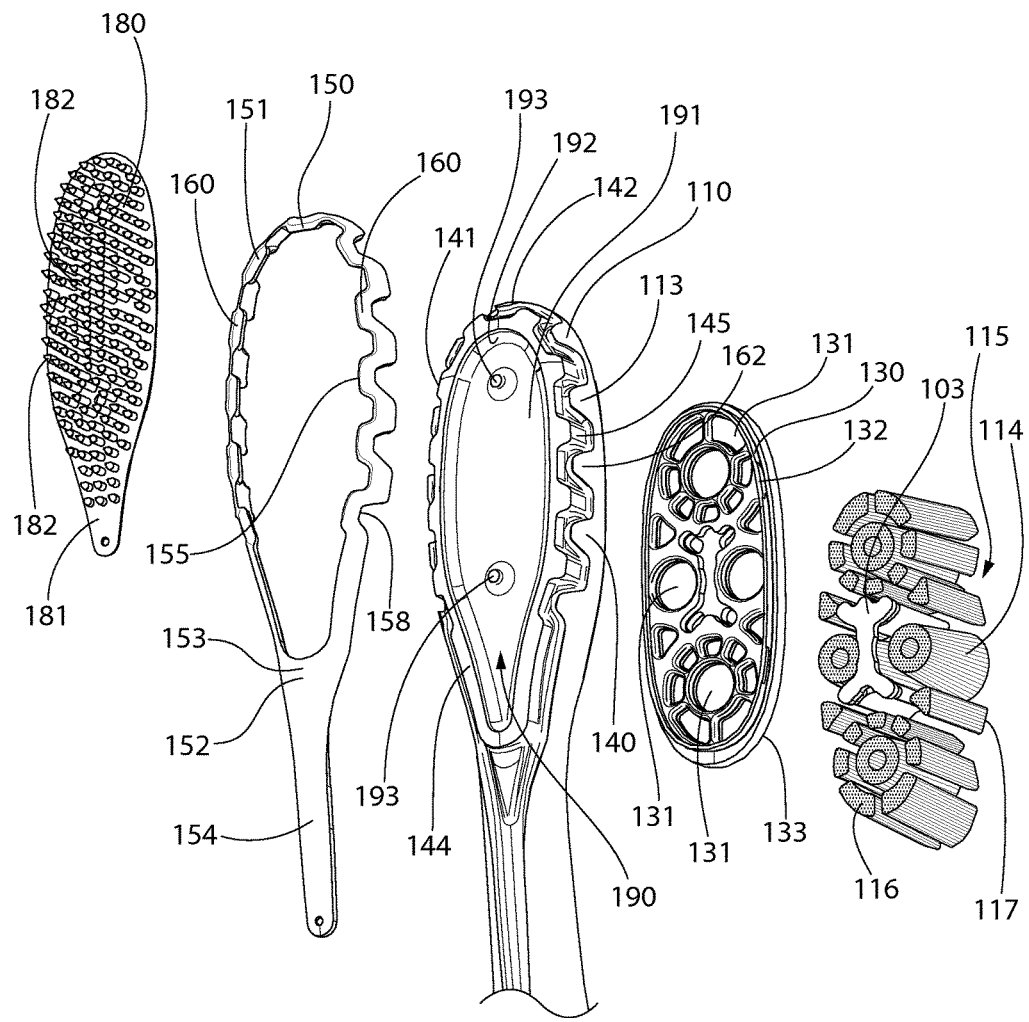
FIG. 4 is an exploded view of a head of the oral care implement of FIG. 1.
Figure 5:
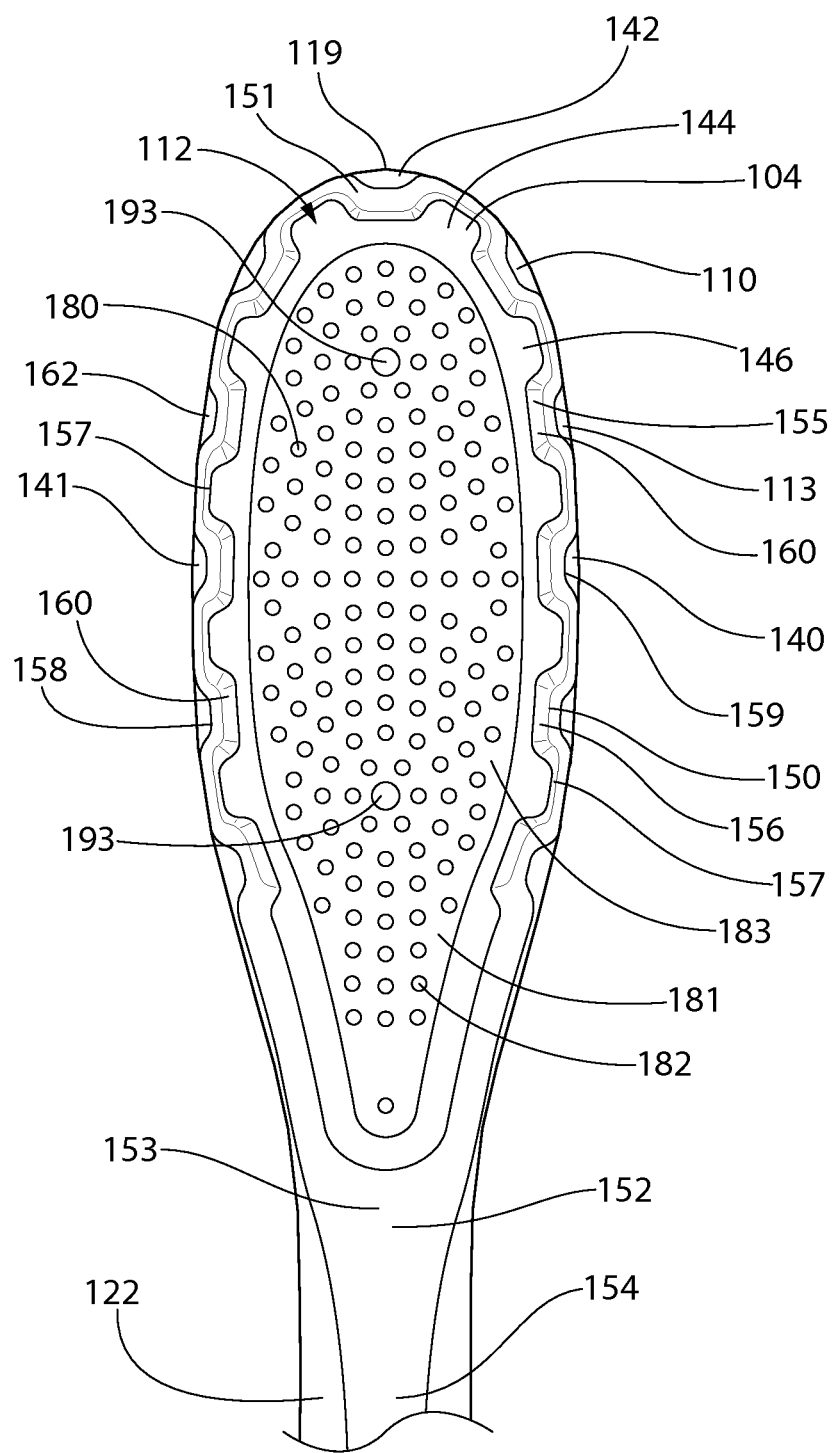
FIG. 5 is a rear view of the head of the oral care implement of FIG. 1.
Figure 7:
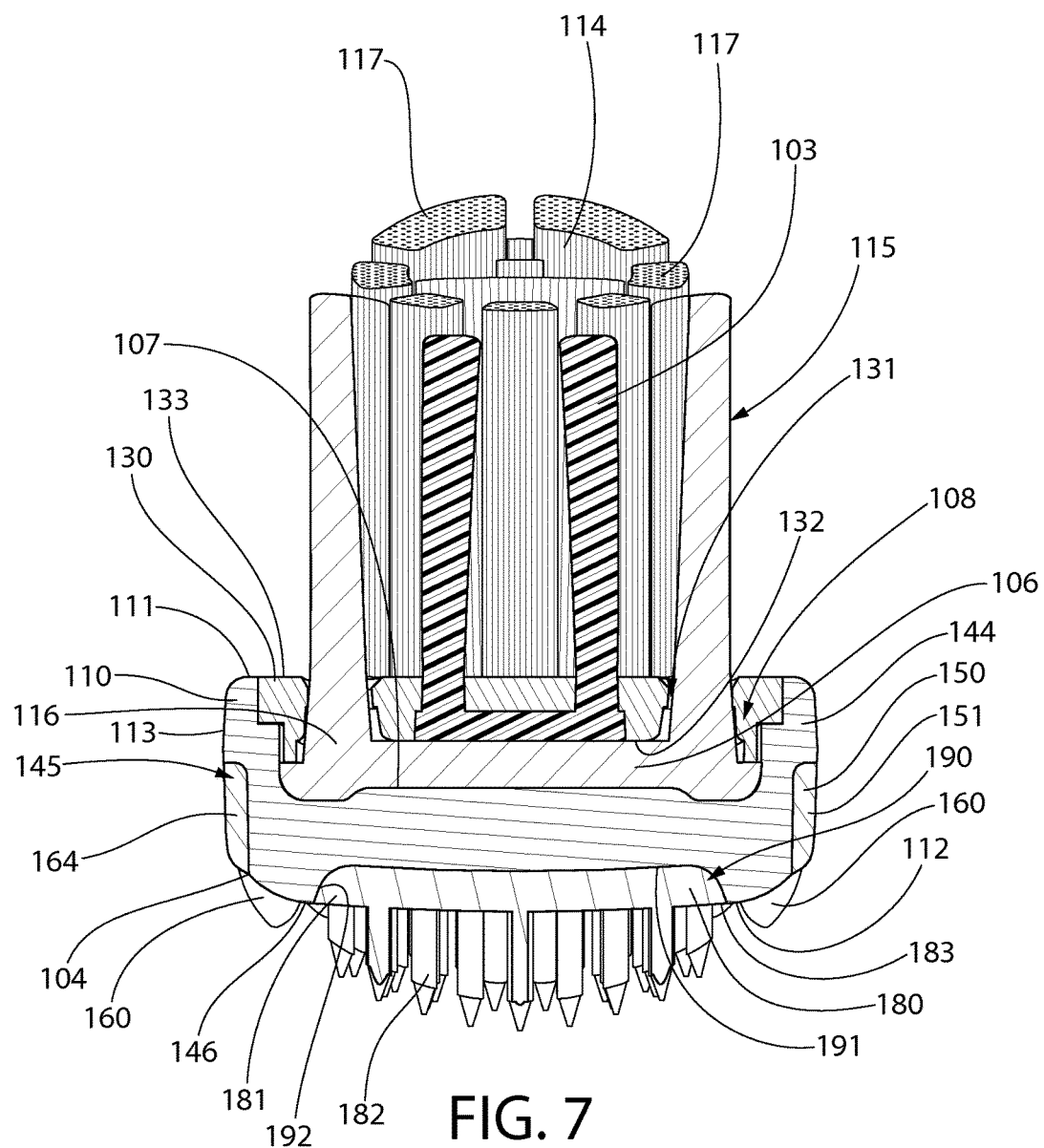
FIG. 7 is a cross-sectional view taken along line VII-VII of FIG. 6.
Figure 8:
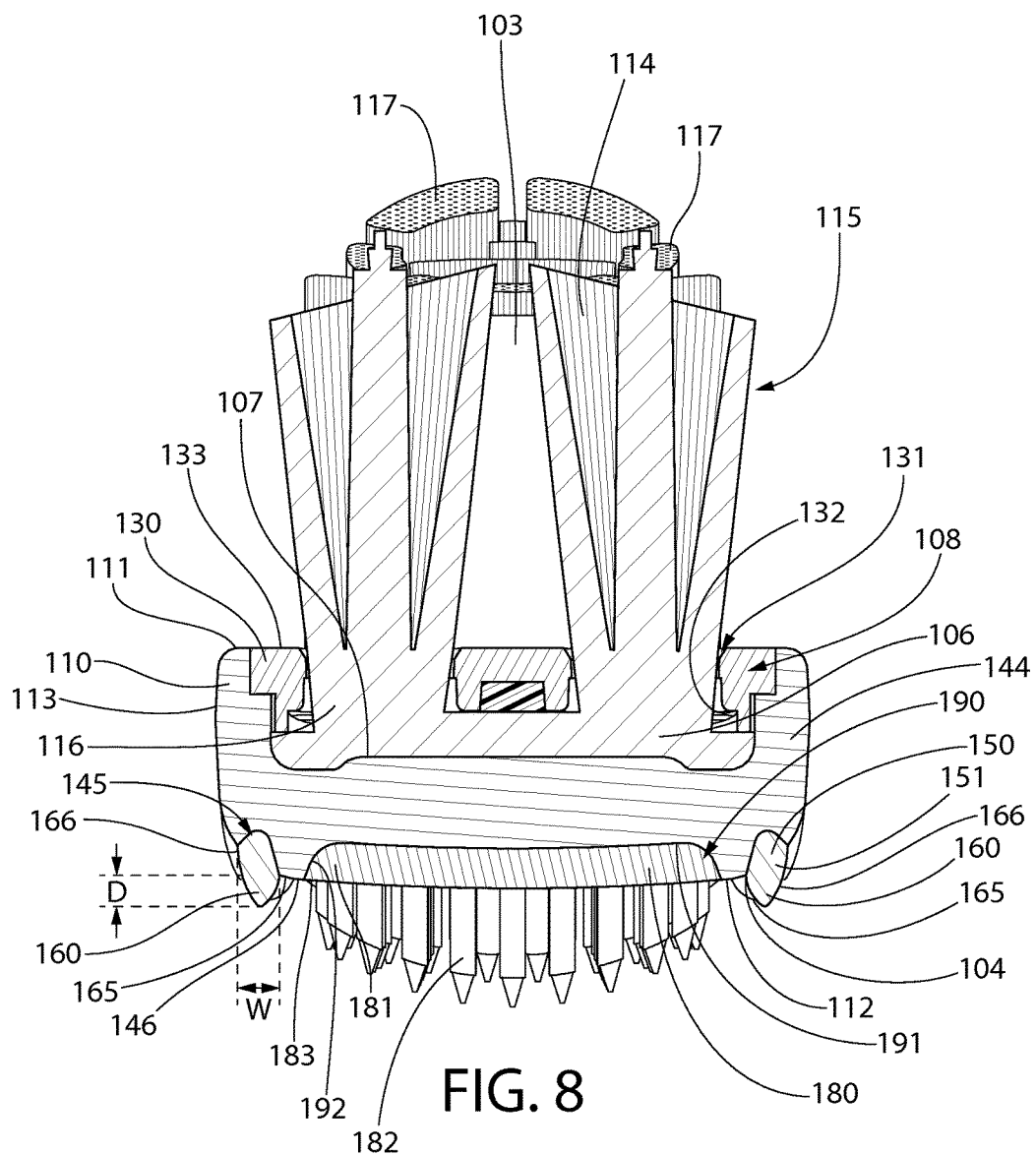
FIG. 8 is a cross-sectional view taken along line VIII-VIII of FIG. 6.

The tooth cleaning elements 115 may be coupled to the head 110 in any manner known in the art, including staples, in-mold tufting (IMT), anchor-free tufting (AFT), or a modified AFT known as AMR. Referring briefly to FIGS. 4, 7, and 8, one manner in which the tooth cleaning elements 115 are secured to the head 110 via AFT will be described. Specifically, in the embodiment exemplified the tooth cleaning elements 115 are formed as a cleaning element assembly on a head plate 130 such that one or more of the tooth cleaning elements 115 are mounted onto the head plate 130 and then the head plate 130 is coupled to the head 110. In such an embodiment, the head plate 130 is a separate and distinct component from the head 110 of the oral care implement 100. However, the head plate 130 is connected to the head 110 at a later stage of the manufacturing process by any suitable technique known in the art, including without limitation thermal or ultrasonic welding, any fusion techniques such as thermal fusion, melting, a tight-fit assembly, a coupling sleeve, threaded engagement, adhesion, or fasteners. Thus, the head plate 130 and the head 110 are separately formed components that are secured together during manufacture of the oral care implement 100.

In certain embodiments, the head plate 130 may comprise an upper surface 133 and a lower surface 132. The upper surface 133 of the head plate 130 forms a portion of the front surface 111 of the head 110 when the head plate 130 is coupled to the head 110 as discussed herein. The head plate 130 comprises a plurality of holes 131 formed therethrough from the upper surface 133 to the lower surface 132, and the tooth cleaning elements 115 may be mounted to the head plate 130 within the holes 131. Specifically, in AFT a plate or membrane (i.e., the head plate 130) is created separately from the head 110. The tooth cleaning elements 115 (such as bristles, elastomeric elements, and combinations thereof) are positioned into the head plate 130 so as to extend through the holes 131 of the head plate 130. The free ends 117 of the tooth cleaning elements 115 on one side of the head plate 130 perform the cleaning function. The anchor portions 116 of the tooth cleaning elements 115 on the other side of the head plate 130 are melted together by heat to be anchored in place. As the tooth cleaning elements 115 are melted together, a melt matte 106 is formed. The melt matte 106 is a thin layer of plastic that is formed by melting the anchor portions 116 of the bristles so that the anchor portions 116 of the bristles transition into a liquid, at which point the liquid of the anchor portions 116 of the bristles combine together into a single layer of liquid plastic that at least partially covers the lower surface 132 of the head plate 130. After the heat is no longer applied, the melted anchor portions 116 of the bristles solidify/harden to form the melt matte 106 or thin layer of plastic.

After the tooth cleaning elements 115 are secured to the head plate 130, the head plate 130 is secured to the head 110 such as by ultrasonic welding or mechanical techniques (i.e., snap-fit, interference fit, slot-and-tab, or the like) so that the upper surface 133 of the head plate 130 forms at least a portion of the front surface 111 of the head 110. When the head plate 130 is coupled to the head 110, the melt matte 106 is located between the lower surface 132 of the head plate 130 and a floor 107 of a basin 108 of the head 110 in which the head plate 130 is disposed. The melt matte 106, which is coupled directly to and in fact forms a part of the tooth cleaning elements 115, prevents the tooth cleaning elements 115 from being pulled through the holes 131 in the head plate 130 to ensure that the tooth cleaning elements 115 remain attached to the head plate 130 during use of the oral care implement 100.

As noted above, in another embodiment the tooth cleaning elements may be connected to the head 110 using a technique known in the art as AMR. In this technique, the handle is formed integrally with the head plate as a one-piece structure. After the handle and the head plate are formed, the bristles are inserted into holes in the head plate so that the free/cleaning ends of the bristles extend from the front surface of the head plate and the bottom ends of the bristles are adjacent to the rear surface of the head plate. After the bristles are inserted into the holes in the head plate, the bottom ends of the bristles are melted together by applying heat thereto, thereby forming a melt matte at the rear surface of the head plate. The melt matte is a thin layer of plastic that is formed by melting the bottom ends of the bristles so that the bottom ends of the bristles transition into a liquid, at which point the liquid of the bottom ends of the bristles combine together into a single layer of liquid plastic that at least partially covers the rear surface of the head plate. After the heat is no longer applied, the melted bottom ends of the bristles solidify/harden to form the melt matte/thin layer of plastic. In some embodiments, after formation of the melt matte, a tissue cleanser is injection molded onto the rear surface of the head plate, thereby trapping the melt matte between the tissue cleanser and the rear surface of the head plate. In other embodiments, other structures may be coupled to the rear surface of the head plate to trap the melt matte between the rear surface of the head plate and such structure without the structure necessarily being a tissue cleanser (the structure can just be a plastic material that is used to form a smooth rear surface of the head, or the like).

Of course, techniques other than AFT and AMR can be used for mounting the tooth cleaning elements 115 to the head 110, such as widely known and used stapling techniques or the like. In such embodiments the head plate 130 may be omitted and the tooth cleaning elements 115 may be coupled directly to the head 110. Furthermore, in a further modified version of the AFT and AMR processes discussed above, the head plate 130 may be formed by positioning the tooth cleaning elements 115 within a mold, and then molding the head plate 130 around the tooth cleaning elements 115 via an injection molding process.

Referring again to FIGS. 1 and 2, in the exemplified embodiment the plurality of tooth cleaning elements 115 includes a plurality of separate tufts of bristles 114 and a plurality of elastomeric tooth cleaning elements 103. Although illustrated herein as having a specific arrangement and shape, the arrangement of the tufts of bristles 114 and elastomeric tooth cleaning elements 103 as well as the shapes thereof can be modified from that which is depicted in the figures. Thus, the collective tooth cleaning elements 115 can be any pattern or arrangement and each one of the tooth cleaning elements 115 can have any desired shape.

Referring to FIGS. 3-8 concurrently, the head 110 of the oral care implement 100 will be described in more detail. As noted above, the head 110 comprises the front surface 111, the rear surface 112 opposite the front surface 111, and the peripheral surface 113 extending between the front and rear surfaces 111, 112. The peripheral surface 113 forms a periphery of the head 110 and defines the outermost boundary of the head 110. The peripheral surface 113 of the head 110 includes a first lateral side portion 140, a second lateral side portion 141 opposite the first lateral side portion 140, and a distal portion 142 extending between the first and second lateral side portions 140, 141. The distal portion 142 of the peripheral surface 113 includes the distal end 119 of the head 110.

The head 110 of the oral care implement 100 comprises a base 144 that is formed of a hard plastic material, such as any of the materials noted above for forming the handle 120 (including polypropylene and the like). Furthermore, the head 110 comprises a first elastomeric soft tissue cleanser 150 and a second elastomeric soft tissue cleanser 180 that are coupled to the base 144. Each of the first and second elastomeric soft tissue cleansers 150, 180 are formed of a resilient and flexible elastomeric material, such as a thermoplastic elastomer. The first and second elastomeric soft tissue cleansers 150, 180 serve to clean the user's tongue and soft tissue surfaces and to protect the user's gums. Specifically, the first elastomeric soft tissue cleanser 150 is positioned on the peripheral surface 113 of the head 110 and thus reduces the impact of the hard plastic of the base 144 against the user's gums during use of the toothbrush. The first elastomeric soft tissue cleanser 150 also includes raised features that protrude beyond the rear surface 112 of the head 110 and can also be used for cleaning/scraping a user's tongue. The second elastomeric soft tissue cleanser 180 is positioned on the rear surface 112 of the head 110 and can be used to clean and scrub a user's tongue and other soft tissue surfaces. The combination of the first and second elastomeric soft tissue cleansers 150, 180 also results in a highly desirable aesthetic appearance for the oral care implement 100.

Figure 3:
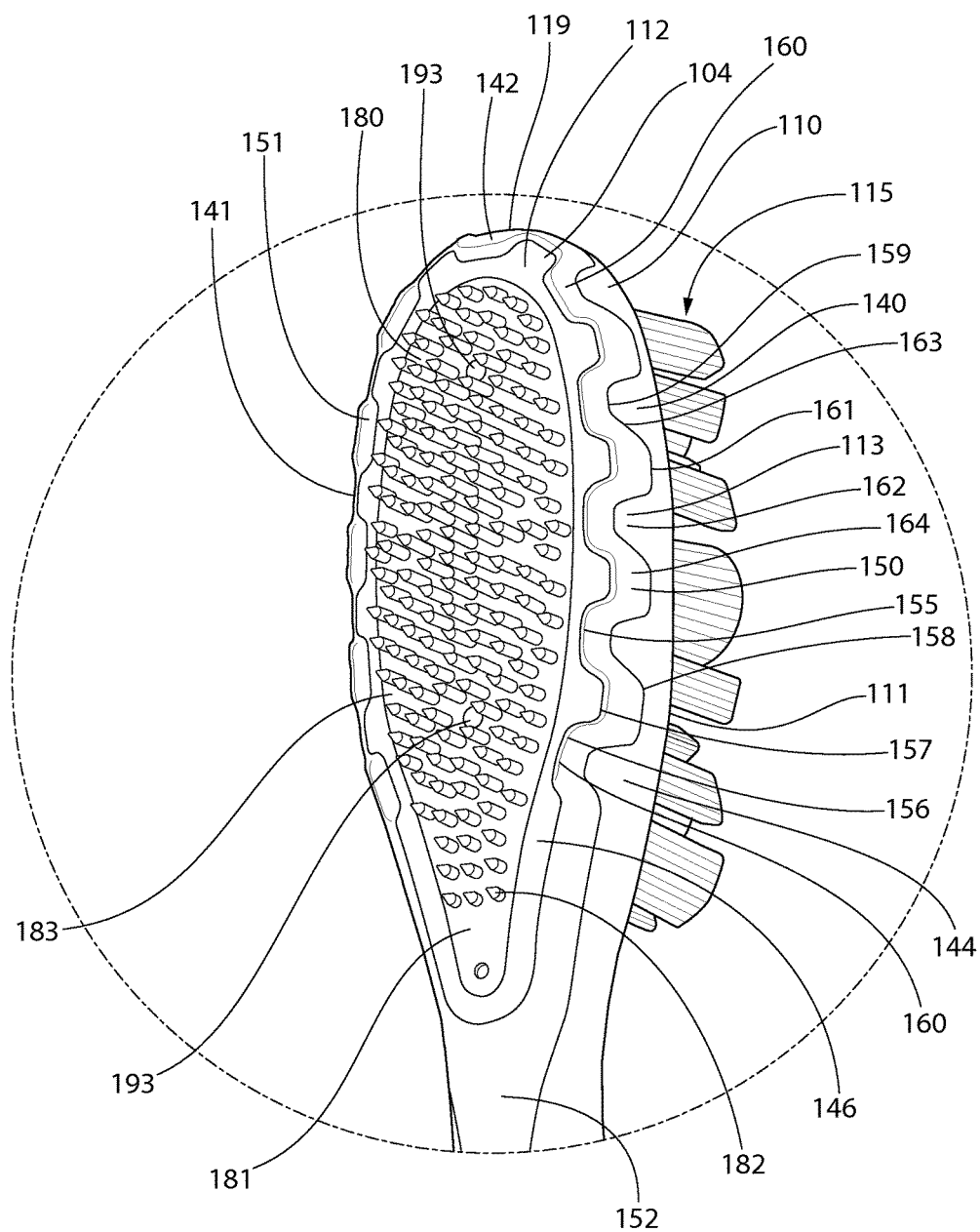
FIG. 3 is a close-up view of area III of FIG. 2.

As noted above, the second elastomeric soft tissue cleanser 180 is coupled to the base 144 of the head 110 on the rear surface 112 of the head 110. The second elastomeric soft tissue cleanser 180 comprises a pad 181 and a plurality of protuberances 182 that extend from the pad 181. In the exemplified embodiment, each of the plurality of protuberances 182 is in the form of a nub. As used herein a "nub" generally refers to a column-like protrusion (without limitation to the cross-sectional shape of the protrusion) which is upstanding from a base surface. In a general sense, the protuberances 182 in the preferred construction have a height that is greater than the width at the base of the protuberance 182 (as measured in the longest direction). Nevertheless, protuberances or nubs could include projections wherein the widths and heights are roughly the same or wherein the heights are somewhat smaller than the base widths. Moreover, in some circumstances (e.g., where the protuberances taper to a tip or include a base portion that narrows to a smaller projection), the base width can be substantially larger than the height. Furthermore, in the exemplified embodiment the plurality of protuberances 182 have varying heights such that some of the protuberances 182 are taller than other of the protuberances 182 (as best seen in FIGS. 3, 7, and 8).

The base 144 of the head 110 comprises a basin 190 formed therein. The basin 190 is defined by a floor 191 that is recessed relative to the rear surface 112 of the head 110 and a sidewall 192 that extends from the floor 191 to the rear surface 112 of the head 110. The second elastomeric soft tissue cleanser 180 is positioned within the basin 190. More specifically, the pad 181 of the second elastomeric soft tissue cleanser 180 is disposed within the basin 190 so that an exposed surface 183 of the pad 181 is flush or substantially flush with the portion of the rear surface 112 of the head 110 that is formed by the base 144 (substantially flush can be the exposed surface 183 of the pad 181 either extending beyond or being recessed relative to the rear surface 112 of the base 144 of the head 110 by between approximately 0.1 mm and 1.0 mm). The exposed surface 183 of the pad 181 thus forms a part of the rear surface 112 of the head 110. Furthermore, the plurality of protuberances 192 extend from the rear surface 112 of the head 110 for contact with a user's soft tissue surfaces. The second elastomeric soft tissue cleanser 180 may be coupled to the head via an injection molding process (i.e., by injection molding an elastomeric material directly into the basin 190 while the head 110 is positioned within a mold). In certain embodiments the head 110 may include one or more peg members 193 that extend upwardly from the floor 191 of the basin 190 to assist in retaining the second elastomeric soft tissue cleanser 180 within the basin 190.

The first elastomeric soft tissue cleanser 150 is a completely separate and distinct component relative to the second elastomeric soft tissue cleanser 180. Thus, in the exemplified embodiment the first and second elastomeric soft tissue cleansers 150, 180 are completely isolated from one another and do not overlap or contact one another at any location. Rather, the first and second elastomeric soft tissue cleansers 150, 180 are isolated from one another by an exposed portion 146 of the base 144 of the head 110. Thus, the first elastomeric soft tissue cleanser 150 may be injection molded to the head 110 in a separate process than the injection molding of the second elastomeric soft tissue cleanser 180. The first elastomeric soft tissue cleanser 150 is also formed of a soft, resilient, and flexible material, such as a thermoplastic elastomer. In certain embodiments the first and second elastomeric soft tissue cleansers 150, 180 may have the same Shore durometer/hardness. In other embodiments the first and second elastomeric soft tissue cleansers 150, 180 may have different Shore durometer/hardnesses (with either of the first and second elastomeric soft tissue cleansers 150, 180 being harder than the other to achieve a desired cleaning effect).

As noted above, the first elastomeric soft tissue cleanser 150 is coupled to the head 110 along the peripheral surface 113 of the head 110. More specifically, the first elastomeric soft tissue cleanser 150 comprises a bumper portion 151 that extends along the peripheral surface 113 of the head 110 and a connecting portion 152 that is located on one or both of the rear surface 112 of the head 110 and a neck portion 122 of the handle 120. The bumper portion 151 of the first elastomeric soft tissue cleanser 150 extends in a continuous manner along each of the first lateral side portion 140 of the peripheral surface 113 of the head 110, the distal portion 142 of the peripheral surface 113 of the head 110, and the second lateral side portion 141 of the peripheral surface 113 of the head 110. Due to the connecting portion 152 of the first elastomeric soft tissue cleanser 150 extending along the rear surface 112 of the head 110 or the neck portion of the handle 120, the bumper portion 151 and the connecting portion 152 of the first elastomeric soft tissue cleanser 150 collectively form an annular structure that surrounds the rear surface 112 of the head 110.

In the exemplified embodiment the connecting portion 152 of the first elastomeric soft tissue cleanser 150 comprises a first section 153 that extends along the proximal portion of the rear surface 112 of the head 110. Thus, the first section 153 of the connecting portion 152 of the first elastomeric soft tissue cleanser 150 extends between the first and second lateral side portions 140, 141 of the peripheral surface 113 of the head 110 and connects the portion of the bumper portion 151 that is positioned on the first lateral side portion 140 to the portion of the bumper portion 151 that is positioned on the second lateral side portion 141. The connecting portion 152 of the first elastomeric soft tissue cleanser 150 also comprises a second section 154 that extends longitudinally along the rear surface of the neck 122 of the handle 120 (see FIG. 2).

As best seen in FIGS. 4, 7, and 8, the base 144 of the head 110 comprises a channel 145 that extends along the first and second lateral side portions 140, 141 and the distal portion 142 of the peripheral surface 113. The channel 145 is a continuous, indented surface feature formed into the base 144 of the head 110 that extends along each of the portions of the peripheral surface 113 of the head 110. The channel 145 has a wave-like, undulating, or sinusoidal shape as it extends along the first and second lateral side portions 140, 141 and the distal portion 142 of the peripheral surface 113. The channel 145 forms a closed-loop because in addition to extending along the first and second lateral side portions 140, 141 and the distal portion 142 of the peripheral surface 113, it also extends along the rear surface of the proximal end of the head 110 or along the neck 122. The first elastomeric soft tissue cleanser 150 is at least partially disposed within the channel 145. Stated another way and as will be better understood from the description below, a first portion of the first elastomeric soft tissue cleanser 150 is disposed in the channel 145 and a second portion of the first elastomeric soft tissue cleanser 150 protrudes from the channel 145.

Still referring to FIGS. 3-8 concurrently, in between the first and second elastomeric soft tissue cleansers 150, 180 the base 144 of the head 110 comprises an exposed annular surface 146. The exposed annular surface 146 of the base 144 forms a portion of the rear surface 112 of the head 110 and it maintains the first and second elastomeric soft tissue cleansers 150, 180 completely separate from one another. In the exemplified embodiment, the exposed annular surface 146 of the base 144 and the exposed surface 183 of the pad 181 of the second elastomeric soft tissue cleanser 180 collectively form the entire rear surface 112 of the head 110.

The exposed annular surface 146 of the base 144 is located adjacent to the peripheral surface 113 of the head 110 and circumscribes the second elastomeric soft tissue cleanser 180. Thus, the first elastomeric soft tissue cleanser 150 circumscribes the exposed annular surface 146 of the base 144 and the exposed annular surface 146 of the base 144 circumscribes the second elastomeric soft tissue cleanser 180. Because the first elastomeric soft tissue cleanser 150 is a continuous structure, the first elastomeric soft tissue cleanser 150 substantially surrounds the exposed annular surface 146 of the base 144. Similarly, because the exposed annular surface 146 of the base 144 is a continuous surface, the exposed annular surface 146 of the base 144 substantially surrounds the second elastomeric soft tissue cleanser 180. As can be seen in the figures, in the exemplified embodiment no portion of the first or second elastomeric soft tissue cleansers 150, 180 traverses or otherwise passes over or along the exposed annular surface 146 of the base 144. Thus, the exposed annular surface 146 of the base 144 is an annular region of the base 144 that is completely devoid of an elastomeric material being coupled or adhered thereto.

As noted above, the bumper portion 151 of the first elastomeric soft tissue cleanser 150 extends continuously along the first and second lateral portions 140, 141 and the distal portion 142 of the peripheral surface 113 of the head 110. The peripheral surface 113 of the head 110 and the rear surface 112 of the head 110 intersect to form a perimeter 104 of the rear surface 112 of the head 110. The bumper portion 151 of the first elastomeric soft tissue cleanser 150 comprises a plurality of raised portions 160 located along the perimeter 104 that protrude above (or protrude beyond) the rear surface 112 of the head 110 and a plurality of lower portions 164 that are located on the peripheral surface 113. Thus, the bumper portion 151 of the first elastomeric soft tissue cleanser 150 extends continuously along the peripheral surface 113 of the head 110 without gaps or breaks and includes the raised portions 160 that protrude beyond the rear surface 112 of the head 110 at the perimeter 104 where the peripheral surface 113 meets/intersects the rear surface 112 and the lower portions 164 that are located on the peripheral surface 113 and do not protrude beyond the rear surface 112 of the head 110.

The bumper portion 151 alternates between the raised portions 160 and the lower portions 164 as it extends along the periphery 113 of the head 110. Thus, the raised portions 160 are spaced-apart along the perimeter 103 of the head 110 and the lower portions 164 are spaced apart along the peripheral surface 113 of the head 110. A portion of the exposed annular surface 146 of the base 144 of the head 110 is located between each pair of adjacent raised portions 160. Thus, the perimeter 104 alternates between the raised portions 160 and the exposed annular surface 146 along the entirety of the perimeter 104 of the head 110. An exposed side surface portion 162 of the base 144 is located between adjacent ones of the lower portions 164 of the bumper portion 151 of the first elastomeric soft tissue cleanser 150. Thus, the peripheral surface 113 alternates between the lower portions 164 and the exposed side surface portion 162 of the base 144 along the entirety of the peripheral surface 113 of the head 110.

The plurality of raised portions 160 protrude beyond the rear surface 112 of the head 110 such that a reference plane that is coextensive with or includes the rear surface 112 of the head 110 will intersect the raised portions 160 of the bumper portion 151 of the first elastomeric soft tissue cleanser 150. The plurality of raised portions 160 are arranged in a spaced-apart manner about the perimeter 104 of the head 110 so as to at least partially circumscribe the rear surface 112 of the head 110.

The bumper portion 151 of the first elastomeric soft tissue cleanser 150 comprises the raised portions 160 on each of the first lateral side portion 140, the second lateral side portion 141, and the distal portion 142. Furthermore, each of the raised portions 160 on the first lateral side portion 140 are transversely aligned with one of the raised portions 160 on the second lateral side portion 141 so that an axis that is perpendicular to the longitudinal axis A-A that intersects one of the raised portion 160 on the first lateral side portion 140 will also intersect one of the raised portions 160 on the second lateral side portion 141. Similarly, each of the lower portions 164 on the first lateral side portion 140 are transversely aligned with one of the lower portions 164 on the second lateral side portion 141. Stated another way, the bumper portion 151 of the first elastomeric soft tissue cleanser 150 is substantially symmetric about the longitudinal axis A-A.

In the exemplified embodiment, the plurality of raised portions 160 of the bumper portion 151 of the first elastomeric soft tissue cleanser 150 are ridges having a length L measured along the perimeter 104 and a width W measured orthogonal to the length L. The length L of each of the plurality of raised portions 160 is greater than its width W. Furthermore, each of the plurality of raised portions 160 protrudes only slightly beyond the rear surface 112 of the head 110, such as between approximately 0.5 mm and 2.0 mm, and more specifically between approximately 0.8 mm and 1.5 mm (indicated in FIG. 8 as protruding distance D). The length L of each of the plurality of raised portions 160 is greater than its protruding distance D. Due to a combination of the length L, width W, and protruding distance D, the raised portions 160 of the bumper portion 151 are somewhat rigid while also being flexible due to being formed of an elastomeric material, which enables the raised portions 160 to gently scrape debris from a user's tongue and other soft tissue surfaces during use.

The protruding distance D of the raised portions 160 of the bumper portion 151 of the first elastomeric soft tissue cleanser 150 is less than the height of at least some (and potentially all) of the protuberances 182 of the second elastomeric soft tissue cleanser 180 (measured from the rear surface 112 of the head 110 to the terminal/distal ends of the protuberances 182). Thus, while the protuberances 182 of the second elastomeric soft tissue cleanser 180 may readily flex and bend when contacted against a user's tongue and other soft tissue surfaces, the raised portions 160 of the first elastomeric soft tissue cleanser 150 will bend to a lesser degree due to the length L and protruding distance D, which enables the raised portions 160 to be used for scraping and penetrating rather than just one or the other.

Of course, the invention is not limited to the raised portions 160 being ridges in all embodiments. In certain other embodiments, the raised portions 160 may be nubs having a protruding distance that is greater than the length and width of the raised portion 160. In such an embodiment the raised portions 160 will be more flexible because a taller, thinner elastomeric structure will have more flexibility than a shorter, thicker elastomeric structure. In certain embodiments it is desirable to have the protruding distance D be less than the length L to minimize the flexibility of the raised portions 160 to increase their ability to scrape a user's tongue and other soft tissue surfaces. Thus, in certain embodiments it is preferred that L>D and L>W.

The raised portions 160 of the bumper portion 151 of the first elastomeric soft tissue cleanser 150 comprise an inner surface 165 facing the second elastomeric soft tissue cleanser 180 and an opposite outer surface 166. In the exemplified embodiment the inner surface 165 is an arcuate surface that extends from a terminal end of the raised portions 160 to the rear surface 112 of the head 110 (and more specifically to the exposed annular surface 146 of the base 144). More specifically, the inner surface 165 is arcuate and convex. The outer surface 166 of the raised portions 160 is also an arcuate and convex surface. More specifically, the outer surface 166 is a continually convex surface from the peripheral surface 113 to the terminal end of the raised portions 160 and the inner surface 165 is a continually convex surface from the rear surface 112 to the terminal end of the raised portions 160. Thus, the inner and outer surfaces 165, 166 of the raised portions 160 are both convex surfaces so that the raised portions 160 have a generally egg-shaped cross-sectional profile (see FIG. 8).

The bumper portion 151 of the first elastomeric soft tissue cleanser 150 comprises an undulating upper edge 155 and an undulating lower edge 158. Each of the undulating upper and lower edges 155, 158 takes on a sinusoidal shape when viewed in side profile. Due to the undulating upper and lower edges 155, 158, the bumper portion 151 of the first elastomeric soft tissue cleanser 150 is also wavy and undulating and has a sinusoidal shape when viewed in side profile.

Figure 6:
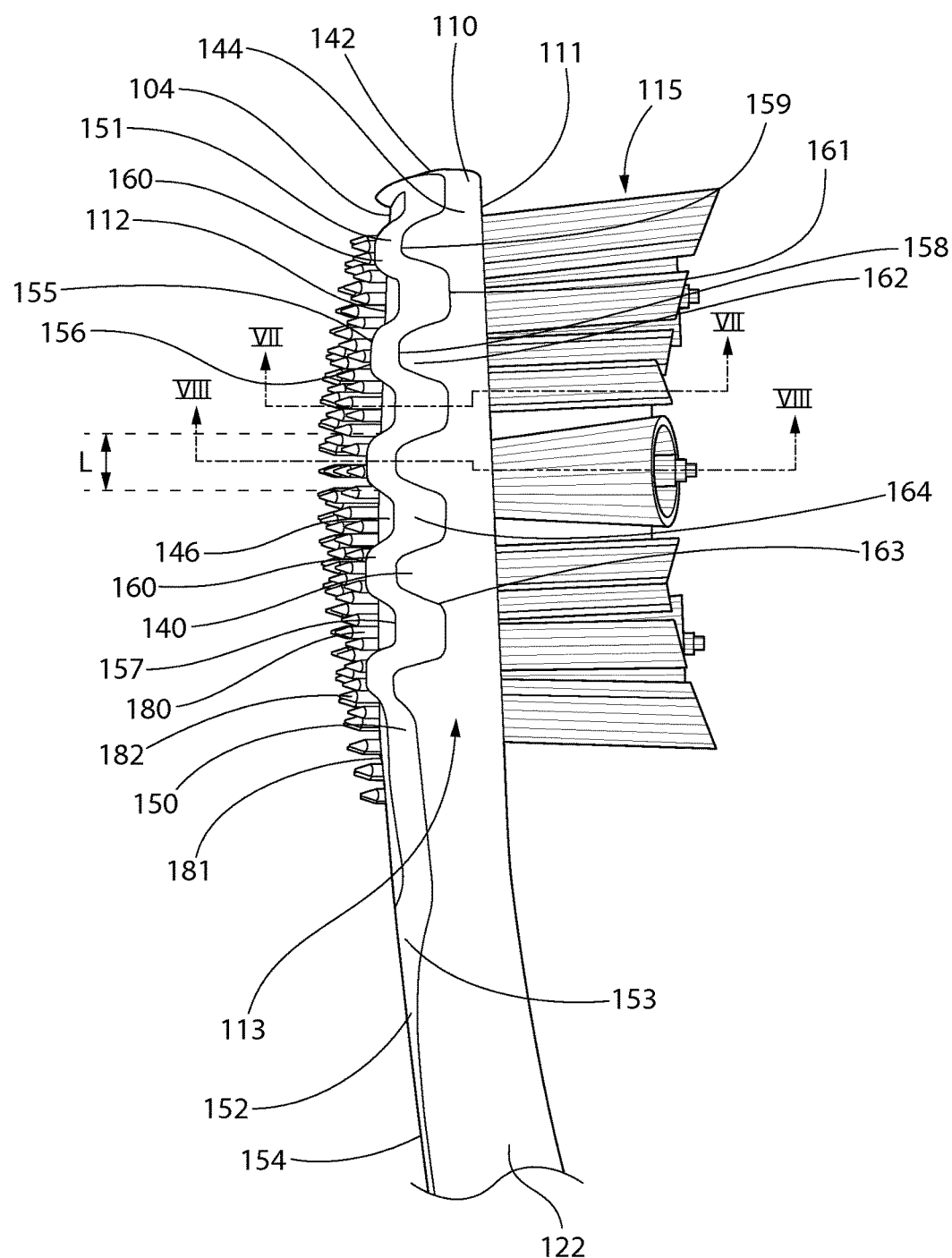
FIG. 6 is a side view of the head of the oral care implement of FIG. 1.

The undulating upper edge 155 of the bumper portion 151 of the first elastomeric soft tissue cleanser 150 includes a plurality of high points 156 that protrude above the rear surface 112 of the head 110 and a plurality of low points 157 that are located at or below the rear surface 112 of the head 110. The protruding appearance of the plurality of high points 156 is best seen in FIGS. 6 and 8. In the exemplified embodiment the plurality of low points 157 of the undulating upper edge 155 are located on the peripheral surface 113 of the head 110 and spaced a distance below the rear surface 113 of the head 110. However, the invention is not to be so limited in all embodiments and the low points 157 of the undulating upper edge 155 may protrude beyond the rear surface 113 in some embodiments, or it may be located right at the perimeter 104 in other embodiments.

The raised portions 160 of the bumper portion 151 of the first elastomeric soft tissue cleanser 150 comprise the high points 156 of the undulating upper edge 155. In the exemplified embodiment the plurality of low points 157 appear to be located below the rear surface 112 of the head 110 and entirely positioned on the peripheral surface 113 of the head 110, but the invention is not to be so limited in all embodiments and the plurality of low points 157 may be located at the rear surface 112 of the head 110 (or directly at the perimeter 104 formed by the intersection of the peripheral surface 113 and the rear surface 112) in other embodiments. The undulating upper edge 155 of the bumper portion 151 of the first elastomeric soft tissue cleanser 150 alternates repetitively between the high points 156 and the low points 157 along the peripheral surface 113 of the head 110.

The undulating lower edge 158 comprises a plurality of high points 159 located on the peripheral surface 113 and a plurality of low points 161 that are also located on the peripheral surface 113. Furthermore, as noted above the base 144 comprises the plurality of exposed side surface portions 162 on the peripheral surface 113. The exposed side surface portions 162 of the base 144 and the lower portions 164 of the bumper portion 151 of the first elastomeric soft tissue cleanser 150 collectively form the peripheral surface 113 of the head 110. Specifically, the undulating lower edge 158 of the bumper portion 151 of the first elastomeric soft tissue cleanser 150 comprises a plurality of valleys 163 that include the low points 161 of the undulating lower edge 158. The exposed side surface portions 162 of the base 144 are located between adjacent ones of the valleys 163 of the undulating lower edge 158.

The high points 156 of the undulating upper edge 155 are aligned with the high points 159 of the undulating lower edge 158. The low points 157 of the undulating upper edge 155 are aligned with the low points 161 of the undulating lower edge 158. In this sense, aligned means that a reference plane that is perpendicular to the longitudinal axis A-A and that extends through the front and rear surfaces 111, 112 of the head 110 will intersect one of the high points 156 of the undulating upper edge 155 and one of the high points 159 of the undulating lower edge 158 or one of the low points 157 of the undulating upper edge 155 and one of the low points 161 of the undulating lower edge 158.

Furthermore, the raised portions 160 of the bumper portion 151 of the first elastomeric soft tissue cleanser 150 are located between the high points 156 of the undulating upper edge 155 and the correspondingly aligned high points 159 of the undulating lower edge 158. The lower portions 164 of the bumper portion 151 of the first elastomeric soft tissue cleanser 150 are positioned on the peripheral surface 113 and in the exemplified embodiment do not protrude beyond the rear surface 112 of the head 110 (although they could in alternative embodiments). The lower portions 164 of the bumper portion 151 of the first elastomeric soft tissue cleanser 150 are located between the low points 157 of the undulating upper edge 155 and the correspondingly aligned low points 161 of the undulating lower edge 158.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:
1. An oral care implement comprising:
a handle; and
a head coupled to the handle, the head comprising:
a front surface;
a rear surface opposite the front surface;
a peripheral surface extending between the rear surface and the front surface;

a first elastomeric soft tissue cleanser comprising a bumper portion, the bumper portion comprising an undulating upper edge and an undulating lower edge that both extend along the peripheral surface of the head, the undulating upper edge forming a plurality of high points projecting outward from the rear surface in a direction opposite the front surface and the undulating lower edge forming a plurality of low points located adjacent the peripheral surface between the front surface and the rear surface; and a plurality of tooth cleaning elements extending from the front surface.

2. The oral care implement according to claim 1 wherein the plurality of high points are spaced from the rear surface of the head in a direction opposite the plurality of tooth cleaning elements.

3. The oral care implement according to claim 1 wherein the first elastomeric soft tissue cleanser comprises a connecting portion on at least one of the rear surface of the head or a neck portion of the handle, the connecting portion and the bumper portion collectively forming an annular structure.

4. The oral care implement according to claim 1 wherein the head comprises a base formed of a hard plastic, the first elastomeric soft tissue cleanser coupled to the base.

5. The oral care implement according to claim 4 further comprising a second elastomeric soft tissue cleanser coupled to the base on the rear surface of the head, the second elastomeric soft tissue cleanser comprising a plurality of protuberances that extend from the rear surface, and the first and second elastomeric soft tissue cleansers being separate and distinct components from one another.

6. The oral care implement according to claim 5 wherein the base comprises an exposed annular surface that forms a portion of the rear surface of the head, the exposed annular surface located adjacent the peripheral surface and circumscribing the second elastomeric soft tissue cleanser.

7. The oral care implement according to claim 5 wherein the base comprises a basin, the second elastomeric soft tissue cleanser comprising a pad portion disposed in the basin.

8. The oral care implement according to claim 5 wherein the base comprises a channel, at least a portion of the first elastomeric soft tissue cleanser disposed in the channel.

9. The oral care implement according to claim 4 wherein the bumper portion comprises an undulating lower edge comprising a plurality of high points located on the peripheral surface and a plurality of low points located on the peripheral surface.

10. The oral care implement according to claim 9 wherein the base comprises a plurality of exposed side surface portions that form portions of the peripheral surface, the exposed side surface portions located between valleys of the undulating lower edge of the bumper portion, the valleys of the undulating lower edge comprising the low points of the undulating lower edge.

11. The oral care implement according to claim 9 wherein the high points of the undulating upper edge are aligned with the high points of the undulating lower edge; and wherein the low points of the undulating upper edge are aligned with the low points of the undulating lower edge.

12. The oral care implement according to claim 1 wherein no portion of the first elastomeric soft tissue cleanser extends beyond the front surface of the head in a direction toward the front surface.

13. The oral care implement according to claim 1 wherein the low points of the undulating upper edge of the bumper portion are located on the peripheral surface and spaced a distance below the rear surface.

14. The oral care implement according to claim 1 wherein the peripheral surface and the rear surface intersect to form a perimeter of the rear surface of the head; and wherein the bumper portion comprises a plurality of raised portions located along the perimeter that protrude above the rear surface, the raised portions comprising the high points.

15. The oral care implement according to claim 14 wherein the raised portions are arranged in a spaced-apart manner about the perimeter so as to at least partially circumscribe the rear surface.

16. An oral care implement comprising:
a handle;
a head coupled to the handle, the head comprising:
    a front surface;
    a rear surface opposite the front surface;
    a peripheral surface extending between the rear surface and the front surface, the peripheral surface and the rear surface intersecting to form a perimeter of the rear surface of the head;
    a base formed of a hard material, the base comprising an exposed annular surface that forms a portion of the rear surface of the head;
    a first elastomeric soft tissue cleanser coupled to the base, the first elastomeric soft tissue cleanser comprising a bumper portion on the peripheral surface, the bumper portion comprising a plurality of lower portions on the peripheral surface and a plurality of raised portions projecting outward from the rear surface along the perimeter in a direction opposite the front surface;
    a second elastomeric soft tissue cleanser coupled to the base on the rear surface of the head, the exposed annular surface of the base circumscribing the second elastomeric soft tissue cleanser, the second elastomeric soft tissue cleanser comprising a plurality of protuberances that extend from the rear surface;
    the first and second elastomeric soft tissue cleansers being separate and distinct components from one another; and
    a plurality of tooth cleaning elements extending from the front surface.

17. The oral care implement according to claim 16 wherein the raised portions of the bumper portion are ridges having a length measured along the perimeter and a width measured orthogonal to the length, the length being greater than the width; and wherein the raised portions are arranged in a spaced-apart manner about the perimeter so as to at least partially circumscribe the rear surface.

18. The oral care implement according to claim 16 wherein the base comprises a basin, the second elastomeric soft tissue cleanser comprising a pad portion disposed in the basin.

19. The oral care implement according to claim 16 wherein the base comprises a channel, at least a portion of the first elastomeric soft tissue cleanser disposed in the channel.

20. An oral care implement comprising:
a handle; and
a head coupled to the handle, the head comprising:
    a front surface;
    a rear surface opposite the front surface;
    a peripheral surface extending between the rear surface and the front surface;
    a first elastomeric soft tissue cleanser comprising a bumper portion that extends along the peripheral surface, the bumper portion comprising an undulating upper edge that includes a plurality of high points and a plurality of low points, the plurality of high points projecting outward from the rear surface in a direction opposite the front surface, and the plurality of low points located adjacent the peripheral surface at or between the front surface and the rear surface; and a plurality of tooth cleaning elements extending from the front surface;

wherein the plurality of high points are spaced from the rear surface of the head in a direction opposite the plurality of tooth cleaning elements and no portion of the first elastomeric soft tissue cleanser extends beyond the front surface of the head.

* * * * *